United States Patent [19]

Rückert

[11] Patent Number: 4,766,081
[45] Date of Patent: Aug. 23, 1988

[54] METHOD FOR THE QUALITATIVE AND QUANTITATIVE DETERMINATION OF THE HYDROGEN ISOTOPES, PROTIUM, DEUTERIUM AND TRITIUM, AND SYSTEM FOR IMPLEMENTING THE METHOD

[75] Inventor: Friedrich Rückert, Karlsruhe, Fed. Rep. of Germany

[73] Assignee: Kernforschungszentrum Karlsruhe GmbH, Karlsruhe, Fed. Rep. of Germany

[21] Appl. No.: 835,989

[22] Filed: Mar. 4, 1986

[30] Foreign Application Priority Data

Mar. 26, 1985 [DE] Fed. Rep. of Germany ....... 3510867

[51] Int. Cl.[4] .................. G01N 21/62; G01N 33/00; G01N 33/18
[52] U.S. Cl. .................................. 436/144; 436/39; 436/171
[58] Field of Search .............. 436/144, 39, 159, 171, 436/182; 422/98

[56] References Cited

U.S. PATENT DOCUMENTS

| | | | |
|---|---|---|---|
| 3,066,220 | 11/1962 | Nief et al. | 436/144 X |
| 3,090,672 | 5/1963 | Von Grotthuss et al. | 436/144 |
| 3,208,826 | 9/1965 | Arnett | 436/144 |
| 3,506,402 | 4/1970 | Simon | 436/39 X |
| 3,945,797 | 3/1976 | Mlinko et al. | 436/144 X |
| 4,066,404 | 1/1978 | Morgan et al. | 436/144 |
| 4,464,338 | 8/1984 | Dotson et al. | 436/39 X |

OTHER PUBLICATIONS

DeLucia et al., Physical Review A, 5 (2), pp. 487–490.
Sugden et al., Microwave Spectroscopy of Gases, D. Van-Nostrand Company, Ltd., 1965, pp. 4–7, 133–134, 146–152, and 191–233.
DeLucia et al., Physical Review A, vol. 8, No. 6, Dec. 1973, pp. 2785–2791.
Helminger et al., Physical Review A, vol. 10, No. 4, Oct. 1974, pp. 1072–1081.

Primary Examiner—David L. Lacey
Assistant Examiner—Jill Johnston
Attorney, Agent, or Firm—Spencer & Frank

[57] ABSTRACT

The present invention relates to a method for the qualitative and quantitative measurement, by means of microwave spectrometry, of the hydrogen isotopes, protium, deuterium and tritium, in a sample which contains hydrogen, water or a mixture thereof, and to an apparatus for implementing the method. Because it is a prerequisite for the use of microwave spectrometry that the isotopes be present in the form of water, and it is advantageous to have impurities in the sample in the form of active or inactive foreign molecules that do not interfere, the present process converts the sample into the gas and/or vapor form. The water vapor component of the sample is subjected to microwave spectrometry and a first measured value compiled, the hydrogen component of the sample is converted to water and then subjected to microwave spectrometry and a second measured value is compiled, whereupon the two measured values are summed to provide the total isotope spectrum. Only the non-condensable gases must be removed. Processing of samples according to the method of the present invention permits the use of microwave spectrometry for the determination of the isotope spectrum in a hydrogen/water mixture.

7 Claims, 2 Drawing Sheets

METHOD FOR THE QUALITATIVE AND QUANTITATIVE DETERMINATION OF THE HYDROGEN ISOTOPES, PROTIUM, DEUTERIUM AND TRITIUM, AND SYSTEM FOR IMPLEMENTING THE METHOD

BACKGROUND OF THE INVENTION

The present invention relates to a method for the qualitative and quantitative determination of the hydrogen isotopes, protium, deuterium and tritium, in a sample that may contain hydrogen, water or a mixture thereof, by means of microwave spectrometry and to a system for implementing the method.

Large quantities of tritium and deuterium are used in nuclear fusion experiments. Water samples containing hydrogen isotopes in greatly varying concentrations must be analyzed. In normal water vapor the percentage of water vapor which contains deuterium and tritium may lie in the ppb or ppm range, but it can also reach up to 100%.

The known detection methods operating with a counting tube or liquid scintillator cannot be used to test samples from nuclear fusion experiments because other $\beta$-radiators interfere with the tests and inactive hydrogen isotopes, protium and deuterium, cannot be detected.

Microwave spectroscopy is generally known, as discussed in "Microwave Spectroscopy of Gases" by T. M. Sugden and C. N. Kenney, 1965, D. VanNostrand Comp., included herein by reference, as is its use for the determination of the structure of molecules, their bond spacing and bond angles. Moreover, the microwave spectrum of the hydrogen compounds $H_2O$, $D_2O$, $T_2O$, HDO, HTO and DTO in a range between 10 GHZ and 300 GHz is known, as disclosed in Physical Review A, Volume 5, 1972, page 487, by DeLucia, Helminger, Cook and Gordy, in Volume 8, 1973, pages 2785–2791 and Volume 10, 1974, pages 1072–1081, by Helminger, DeLucia and Gordy, also included herein by reference.

The microwave spectrum of the hydrogen compound $D_2O$ is known, as disclosed in J. Chem. Phys. 53, 1970, page 2565, by Benedict, Clough, Frenkal and Sullivan and for HDO in J. Chem. Phys. 55, 1971, page 5334, by DeLucia, Cook, Helminger and Gordy.

Teflon ®, which is customarily used as a supporting structure of the Stark electrode in the measuring cell of a microwave spectrometer, absorbs tritium in hydrogen as well as in water form, which negatively influences the lower detection limit. Accordingly, conventional measuring cells cannot be used for detecting and quantifying isotopes of hydrogen.

SUMMARY OF THE INVENTION

It is the object of the present invention to provide an easily implemented detection method for the hydrogen isotope spectrum in samples, which furnishes reliable results, regardless of great fluctuations in the concentrations of the hydrogen isotopes and the presence of inactive and active impurities.

These objects were accomplished based on the recognition that the isotope spectrum of hydrogen and its isotopes in water can be quantitatively and qualitatively measuring using microwave spectrometry. Accordingly, the present invention relates to the measurement of samples of water and its isotopes and, either separately or at the same time, measurement of samples of non-oxidized hydrogen and its isotopes by converting the latter to water by oxidization in the presence of a catalyst before measuring the isotope spectrum using microwave spectrometry.

The water component in the original sample can be separated from the hydrogen component and other gaseous components in an evaporated sample by condensation. Similarly, water in the product of catalytic oxidation can be separated from any non-condensable components in the product in the same manner. The isotope spectra of the original water component and the hydrogen gas component can be determined for each of these fractions in a microwave spectrometer. The total microwave spectra of hydrogen and its isotopes in a sample can be obtained by summing the spectra of the measurement of the original water component and the oxidized hydrogen component, or, alternatively, by treating the entire evaporated original sample by exposure to the oxidation catalyst in combination with oxygen or an oxidation agent, and then conveying the entire stream to the microwave spectrometer for analysis.

DESCRIPTION OF THE PREFERRED EMBODIMENTS

Figure 1:
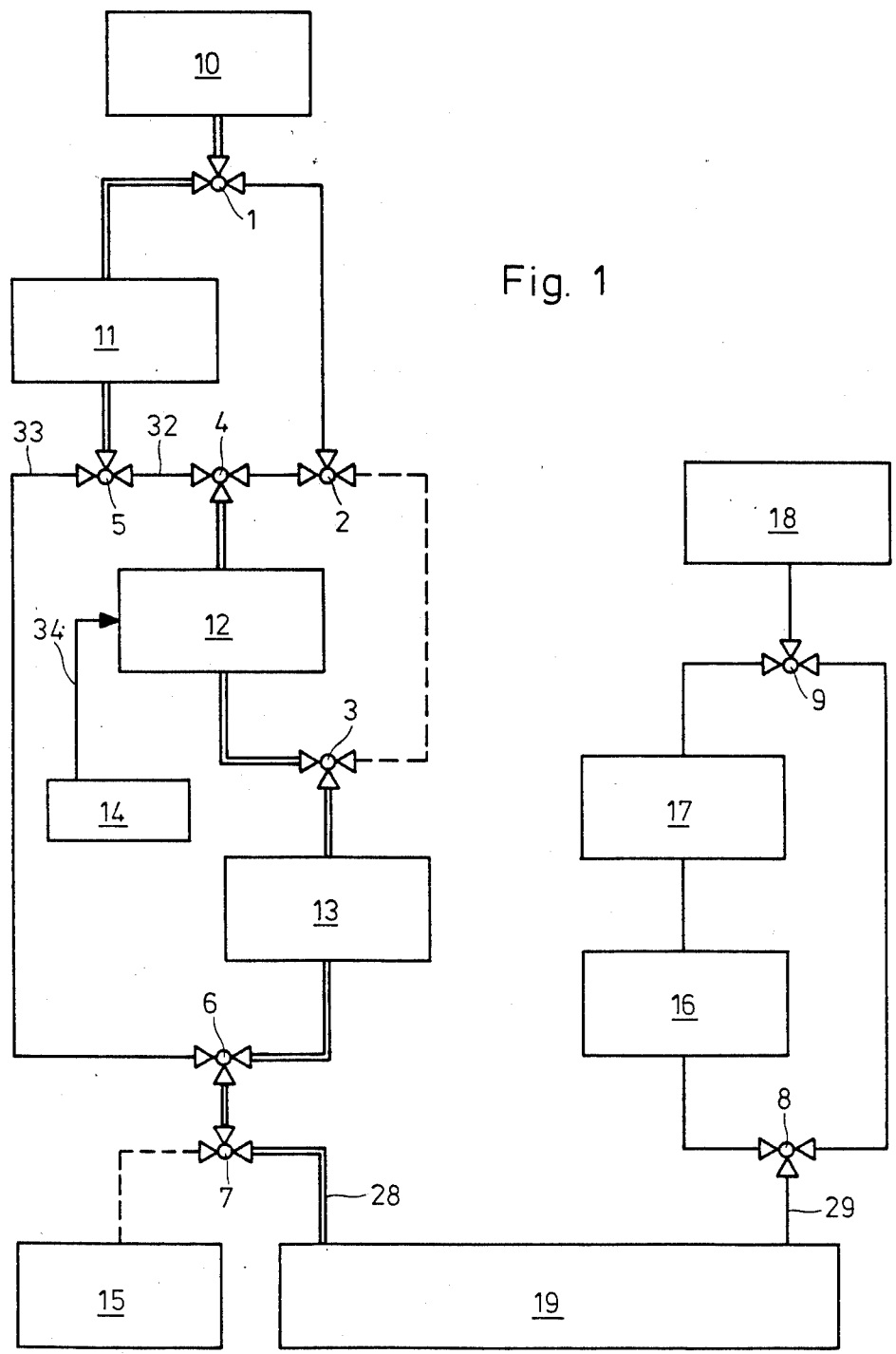
FIG. 1 is a block flow diagram of the process of the invention showing by representation of three-way valves the locations in the flow path of the process that may be altered in order to follow various alternative embodiments of the claimed process.

According to the method of the invention, the sample is first evaporated. If the hydrogen isotopes present in the water component of the sample are to be separately determined, that portion of the evaporated sample is separated by condensation, preferably by cooling. The non-condensed portion, comprising hydrogen and other non-condensable gases, is removed. The condensed water component is again evaporated and conveyed to a microwave spectrometer, where the isotope spectrum is determined.

Hydrogen isotopes present in the non-condensable gases, the hydrogen component, may be determined by reacting that portion of the sample with oxygen or an oxidation agent, preferably in the presence of an oxidizing catalyst. After oxidation, the sample is condensed, preferably by cooling, the non-condensable gases removed, and the condensed water product of oxidation is vaporized and conveyed to a microwave spectrometer, where the isotope spectrum of the hydrogen component of the sample is determined.

Hydrogen is oxidized to water by means of elemental oxygen preferably with the assistance of a platinum catalyst maintained at a temperature above 100° C. to prevent condensation on the catalyst of the water forming. The carrier material of the catalyst must be temperature resistant. Commonly used chemical catalysts may be employed for this purpose, such as platinum on aluminum oxide, asbestos, etc. A catalyst containing 5% of platinum on $\alpha$-aluminum oxide and, in addition, impregnated with silanes (supplied by Degussa) so as to be water-repellent which was used at a temperature of 110° C., performed satisfactorily.

There is also the possibility to oxidize hydrogen by means of copper oxide (CuO) without any addition of elemental oxygen. For this purpose, the hydrogen is passed through a pipe heated to more than 120° C., which contains a sufficient quantity of finely dispersed copper oxide.

To obtain the total isotope quantity and characterization for the original sample, the two isotope spectra determined as above are summed.

If only the isotope characterization of the water component of the sample is desired, of course, only the first condensation and separation step and vaporization of the condensed water component need be performed.

If only a total figure is desired, the entire sample can be treated in the oxidation step without performing the first condensation and separation step.

By any of these embodiments, non-condensable gas impurities that may interfere with the measurement are removed before the microwave spectrometer test.

The advantages realized with the system developed for implementation of the method of the invention are, in particular, that all species of isotopes in the form of water ($H_2O$, HDO, HTO, $D_2O$, TDO, $T_2O$) can be detected directly and those in hydrogen or elemental form ($H_2$, HD, HT, $D_2$, TD, $T_2$) can be detected indirectly after conversion to water. Moreover, these isotopes can be measured at low concentrations in very small samples, i.e., concentrations as low as $10^{-2}$ ppm can be measured in samples as small as $10^{-7}$ mol. The lower detection limit for isotopes thus lies at $10^{-15}$ mol for some species and covers a wide measuring range of from $10^{-2}$ ppm to 100%, with impurities, such as tritized hydrogen, ammonia and methane, as well as radioactive additives, having no adverse influence on the measurement.

Other than hydrogen being converted to water, there are no further changes in the samples. The microwave spectrometer can be operated safely.

The present invention will now be described in greater detail with reference to embodiments illustrated in FIGS. 1 to 3.

FIG. 1 is a flow scheme for an advantageous embodiment of the method defined in claim 1. The functions of the three-way valves employed as switching members, valves 1 to 9, can also be performed by manually operated or automatic blocking members in the intake conduits.

The essentially gaseous and liquid components of a sample, such as hydrogen and water, are converted in evaporator 10 to a hydrogen/water vapor mixture. The hydrogen/water vapor mixture leaving evaporator 10 is conducted, by means of valve 1, through a first, heatable cooling trap 11 where the condensable component, the water, is separated and the uncondensable component, the hydrogen, is fed to a catalyst chamber 12 via valve 5 and valve 4 through line 32. In catalyst chamber 12, oxygen 14 is introduced via oxygen line 34 to oxidize the hydrogen to water, which is then conducted through valve 3 to a second heatable cooling trap 13, where the water formed from hydrogen is condensed. The uncondensable components, essentially the excess oxygen, are extracted through line 33 via valves 6 and 7 by means of an auxiliary pump 15.

The first heatable cooling trap 11 now contains the water component of the sample and the second heatable cooling trap 13 contains the hydrogen component, but in the form of water. Measuring cell 19 is evacuated by means of a high vacuum pump 18 through line 29 via valves 8 and 9. Valves 5, 6 and 7 and line 28 are used to establish a connection between the first heatable cooling trap 11 and measuring position 19, and cooling trap 11 is then heated until the steam pressure required for the measurement is present in measuring cell 19.

The isotope spectrum of the water component of the sample is determined as the first measured valve, after which measuring cell 19 is again emptied via outlet line 29 through valve 8, a third cooling trap 16 and a gas reservoir 17.

Once measuring cell 19 has again evacuated, the second cooling trap 13 is connected with the measuring cell via valves 6 and 7 and line 28. The second cooling trap 13 is heated until the steam pressure inside measuring cell 19 required for the measurement has been reached. The isotope spectrum of the hydrogen component of the sample in the form of water is determined as the second measured value and measuring cell 19 is again emptied, as after the first measurement.

The sum of the two measured values provides the entire isotope spectrum of the sample.

If only the total isotope spectrum is to be determined, and the separate characteristics of the hydrogen isotopes in the gas component or in the water component are not of interest, it is sufficient to take only one measurement. In this case, the sample is conveyed downstream from the evaporator 10, bypassing the first cooling trap 11, directly to catalyst chamber 12 via valves 1, 2 and 4. The hydrogen component of the superheated hydrogen/water vapor mixture is oxidized in catalyst chamber 12. The mixture leaving catalyst chamber 12, essentially composed of water vapor and excess oxygen, is conducted via valve 3 and the second cooling trap 13, with the condensable portion, the water, being separated from the mixture and the uncondensable and interfering component, primarily oxygen, being extracted by means of auxiliary pump 15 through valves 6 and 7. Then the water is evaporated again by being heated in second cooling trap 13 and the isotope spectrum is measured.

If the isotope spectrum of only the water component of the sample is to be determined, the hydrogen component is not oxidized. In this embodiment, evaporator 10 is connected, via valves 1, 2 and 3, directly with second cooling trap 13, avoiding first cooling trap 11 and catalyst chamber 12. Accordingly, the first cooling trap 11 as well as the second cooling trap 13 may be used alternatingly, increasing the rate of measurements. Of course, in this embodiment the hydrogen component is extracted by means of auxiliary pump 15 and is no longer available for measurement.

Figure 2:
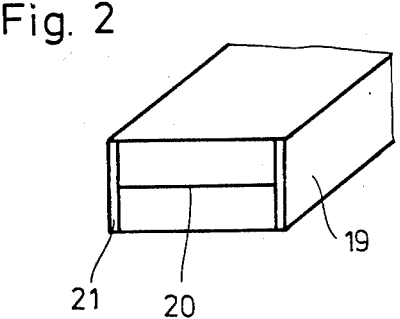
FIG. 2 is a cross-sectional representation of a wave guide measuring cell of a microwave spectrometer.

FIG. 2 is a cross-sectional view of the measuring cell 19 of a microwave spectrometer having a Stark electrode 20 in its interior. The supporting structure 21, which is normally made of Teflon ® in a microwave measuring cell, is made of ceramic material in the present invention. Ceramic supports offer the advantage, unlike Teflon ®, that no hydrogen or its isotopes are absorbed by the supporting material, which would otherwise falsify the measurement. Teflon ® is known to absorb hydrogen and its isotopes, primarily tritium.

Thus, measuring cell 19 only becomes usable for sensitive measurements by the use of ceramic materials for the supporting structure 21.

The stark electrode 20 is insulated electrically from the measurement cell 19 preferably by a layer of aluminum oxide 21. Aluminum oxide is used very successfully in UHV systems, such as the measurement probes of mass spectrometers, to suppress memory effects.

Figure 3:
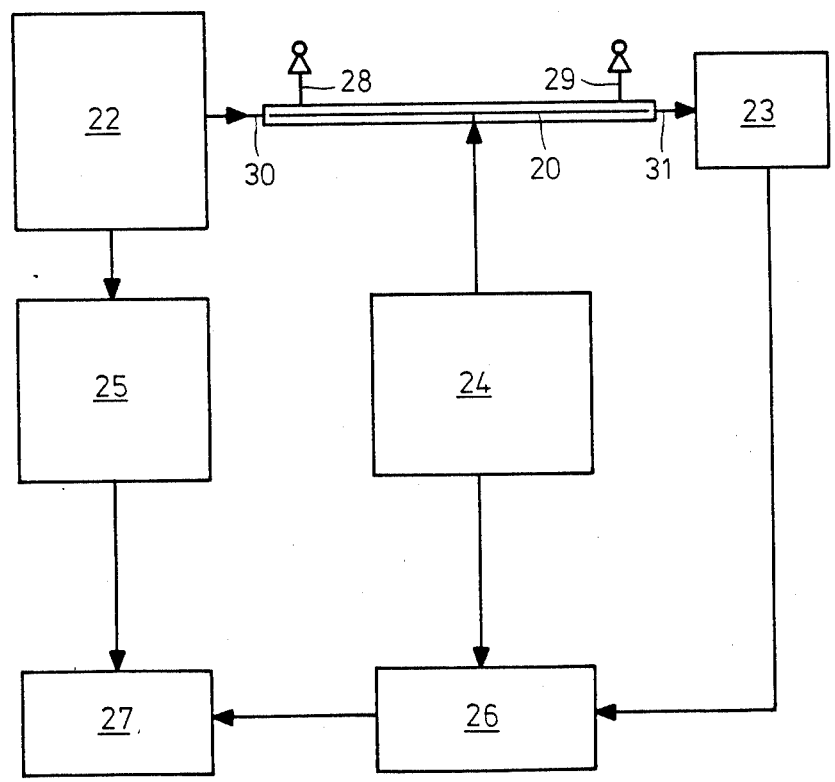
FIG. 3 is a block circuit diagram of a microwave spectrometer measuring device.

FIG. 3 is a block circuit diagram for a measuring device as it is customarily used for microwave spectrometry.

Measuring cell 19 is composed of a long waveguide which is filled, through line 28, with water vapor from the first or second cooling trap (11 or 13) until the required measuring pressure is reached. Microwave input 30 connects measuring cell 19 to the output of a microwave generator 22. A detector 23 for receiving the microwaves passing thorugh measuring cell 19 is disposed at output 31. Detector 23 is followed by a lock-in amplifier 26 which, like the Stark electrode 20, is set at 100 kHz by a generator 24. The fedin frequency is measured by means of a frequency meter 25. The output signals of the lock-in amplifier 26 and of frequency meter 25 are fed to an output unit 27 for generating the spectrogram.

The microwave spectrum of a chemically pure substance, e.g., water,is given by the sum total of the spectra of the isotopic species contained in it. For instance, the spectrum of natural water contains as the main peaks the spectrums of $H_2O$ ($^1H^1HO$)and in addition—with lower intensity (corresponding to the low natural abundance of deuterium (D, $^2H$))—the spectrum of HDO ($^1H^2HO$). The spectra of $H_2O$ and HDO are completely independent of each other. They are made up of a multiplicity of peaks at a variety of frequencies. As a consequence of the high resolution of peaks in microwave spectroscopy, the statistical probability of two peaks of different single spectra coinciding is practically nil. Similar conditions prevail when additional isotopic species (HTO, $T_2O$, DTO, $D_2O$) are present in the measurement gas. The spectra of each of the six isotopic species of water were measured.

It is sufficient, therefore, to select a peak from the spectra of each of these six isotopic species.

These six peaks must meet the following criteria:
(1) For technical reasons they should be located at similar micorwave frequencies. A suitable range of measurement in which peaks of all six isotope combinations can be found is the range between 40 and 60 GHz.
(2) Their peak strengths should be as high as possible.

In this way, the intensities of each of these six peaks selected are a measure of the partial pressures of the associated isotopic species in the measurement space.

Measurement Temperature and Measurement Pressure

The measurement temperature and the measurement pressure may be selected independent of each other within wide limits. However, once selected, they must be kept constant.

Suitable levels, e. g., are 80° C. and $10^{-2}$ mbar.

Calibrating the Microwave Monitor

Once the pressure, temperature, and one peak each for each of the six isotopic combinations have been selected, the monitor can be calibrated. This can be done in two ways:

(1) By plotting a calibration curve

For each of the isotopic species the measured intensity of the peak selected for this purpose is plotted in a diagram as a function of the respective partial pressure. The partial pressure in this case is defined, e. g., by complete evaporation of a sample of known composition at the measurement pressure.

(2) By calculation

The peaks selected for each isotopic species normally will not be of the same type of transition. Normalization to a "normal peak" (reference peak) can be achieved by calculation of the peak strength on the basis of the different zero point energies.

Unknown samples can be analyzed by determining the signal intensities for each of the six peaks selected. In pure samples, a (very intense) signal is obtained for only one of these six peaks. In mixed samples, the different signal intensities of the six peaks plotted versus the calibration curves indicate the respective partial pressures.

The peak spectrum of water is particularly intense. As electronic signal amplification normally can be varied over at least eight orders of magnitude, the limit of detection is determined by the amplification ration in the measurement of the pure sample and the amplification at which the respective peak can just be distinguished from electronic noise. In computer-assisted measurements even those peaks can be made visible by long-time measurements whose intensities are of the order of the electronic noise.

To what extent Teflon ® or ceramic materials are used as insulations of the Stark electrode has no bearing on the measurement. However, ceramic materials are able to reduce drastically the memory effect resulting from poreless processing, thus allowing even samples of very different concentrations to be measured consecutively at short intervals without any falsification arising from previous samples.

It will be understood that the above description of the present invention is susceptible to various modifications, changes and adaptations, and the same are intended to be comprehended within the meaning and range of equivalents of the appended claims.

What is claimed is:

1. A method for the qualitative and quantitative measurement of protium, deuterium and tritium in a sample comprising hydrogen or water or a mixture thereof, comprising:

evaporating any water in the sample to form a first gaseous phase material containing a water vapor component;

conveying the first gaseous phase material to a measuring cell of a microwave spectrometer;

measuring an isotope microwave spectrum of the first gaseous phase material to obtain a first measured value;

oxidizing any protium, deuterium, and tritium in the first gaseous phase material and evaporating said oxides to form a second gaseous phase and material containing water vapor;

conveying said second gaseous phase material to a measuring cell of a microwave spectrometer;

measuring an isotope microwave spectrum of said second gaseous phase material to obtain a second measured value; and subtracting said first measured value from said second measured value to obtain a qualitative and quantitative measurement of protium, deuterium and tritium in said sample.

2. The method of claim 1, wherein the oxidation of protium, deuterium or tritium to a water product is effected by reaction with oxygen or an oxidizing agent in the presence of an oxidation catalyst.

3. The method of claim 1, wherein the sample comprises both a hydrogen component and a water component, comprising the additional steps of condensing the water vapor component from the first gaseous phase material, separating the condensed water vapor component from the non-condensed component of the first gaseous phase material; evaporating the separated water vapor component; conveying the evaporated water vapor component as a separate stream to the measuring cell of the microwave spectrometer; and measuring the isotope spectrum of the water vapor component; thereby obtaining a measurement of all protium, deuterium and tritium in the water component.

4. The method of claim 3, wherein the water vapor component of said first gaseous phase material is condensed by temperature reduction to separate it from the hydrogen component.

5. The method of claim 3, wherein the noncondensed component of the first gaseous phase material is oxidized to convert all protium, deuterium and tritium to a water product; the water product so formed is condensed; the condensed water product is separated; the separated water product is evaporated and the evaporated water product is conveyed to the measuring cell of a microwave spectrometer; and the isotope spectrum of the evaporated water product is measured; thereby obtaining a measurement of all protium, deuterium and tritium in the hydrogen component.

6. The method of claim 5, wherein the protium, deuterium and tritium in the hydrogen component are oxidized to water product by reaction with oxygen or an oxidizing agent in the presence of an oxidation catalyst.

7. The method of claim 5, wherein the measurement obtained for the water component of said first gaseous phase material is added to the measurement obtained for the hydrogen component to determine the total measurement of all protium, deuterium and tritium present as hydrogen or as water in the original sample.

* * * * *